United States Patent [19]

Zamierowski

[11] Patent Number: 5,100,396
[45] Date of Patent: * Mar. 31, 1992

[54] FLUIDIC CONNECTION SYSTEM AND METHOD

[76] Inventor: David S. Zamierowski, 8500 Reinhardt, Leawood, Kans. 66206

[*] Notice: The portion of the term of this patent subsequent to Nov. 13, 2007 has been disclaimed.

[21] Appl. No.: 504,598

[22] Filed: Apr. 3, 1990

Related U.S. Application Data

[63] Continuation-in-part of Ser. No. 332,699, Apr. 3, 1989, Pat. No. 4,969,880.

[51] Int. Cl.$^5$ ............................................. A61F 13/00
[52] U.S. Cl. ........................................ 604/305; 604/180; 604/352; 604/174
[58] Field of Search ............................. 604/174–176, 604/179, 180, 304–305, 307, 313, 26, 49, 352; 128/DIG. 26, 156, 155

[56] References Cited

U.S. PATENT DOCUMENTS

| | | | |
|---|---|---|---|
| 2,547,758 | 1/1949 | Keeling | 604/174 |
| 3,367,332 | 2/1968 | Groves | |
| 3,682,180 | 8/1972 | McFarlane | |
| 4,080,970 | 3/1978 | Miller | 604/174 |
| 4,261,363 | 4/1981 | Russo | 604/174 |
| 4,275,721 | 6/1981 | Olson | |
| 4,373,519 | 2/1983 | Errede et al. | |
| 4,382,441 | 5/1983 | Svedman | |
| 4,392,853 | 7/1983 | Muto | 604/180 |
| 4,419,097 | 12/1983 | Rowland | 604/174 |
| 4,480,638 | 11/1984 | Schmid | |
| 4,525,166 | 6/1985 | Lechers | |
| 4,540,412 | 9/1985 | Van Overloop | |
| 4,543,100 | 9/1985 | Brodsky | |
| 4,605,399 | 8/1986 | Weston et al. | |
| 4,608,041 | 8/1986 | Nielson | |
| 4,640,688 | 2/1987 | Hauser | 604/180 |
| 4,743,232 | 5/1988 | Kruger | |
| 4,775,909 | 10/1988 | Eisenburg | |
| 4,838,883 | 6/1989 | Matsuura | |
| 4,840,187 | 6/1989 | Brazier | |
| 4,863,449 | 9/1989 | Therriautt et al. | |
| 4,878,901 | 11/1989 | Sachse | 604/174 |
| 4,969,880 | 11/1990 | Zemierowski | 604/180 |

Primary Examiner—C. Fred Rosenbaum
Assistant Examiner—Chalin Smith
Attorney, Agent, or Firm—Litman, McMahon & Brown

[57] ABSTRACT

A fluidic connection system includes a membrane with an inner contact surface, an outer surface, and a pair of cover panels with perimeters, interior portions and edge strips. The panels are joined together at a seam extending transversely along their edge strips. A tube opening extends between the edge strips and is open at the membrane inner and outer surfaces. A tube or sheath includes a proximate end extending through the tube opening and terminating at the membrane inner surface and a distal end terminating in spaced relation from the membrane outer surface. Adhesive is applied to the membrane inner contact surface for releasably fastening the membrane on a patient's skin. The system can be utilized as a wound dressing for draining wound exudate and for introducing liquid, e.g. growth factors and antibiotics, to the wound site. The membrane can comprise a semi-permeable material. In one embodiment the tube proximate end includes a side opening and extends through the membrane tube opening for placement adjacent to an inner skin contact surface. In another embodiment the tube proximate end is split to form a pair of opposed tabs, each of which is attached to a membrane panel. The tabs form a proximate end opening or mouth of the tube. The membrane panels can be adhesively secured to a patient's penis for using the system as a condom catheter.

29 Claims, 4 Drawing Sheets

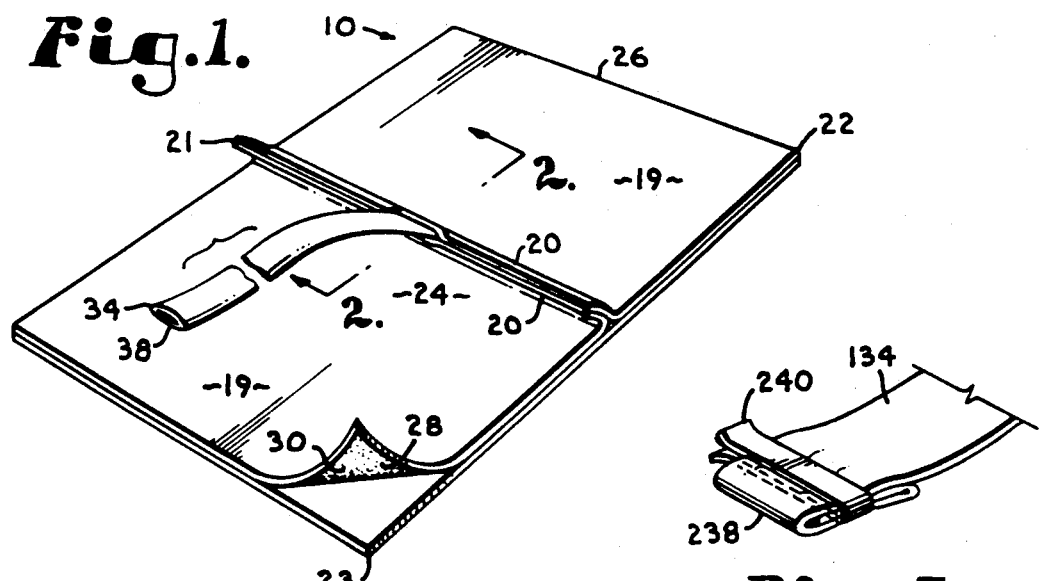
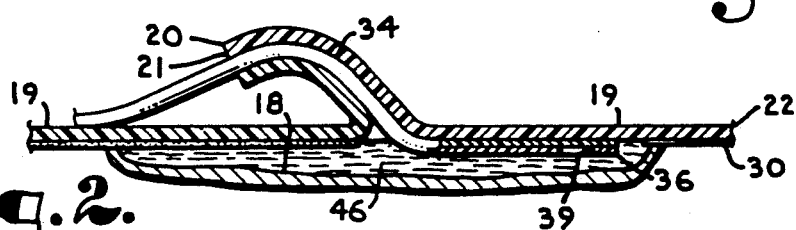
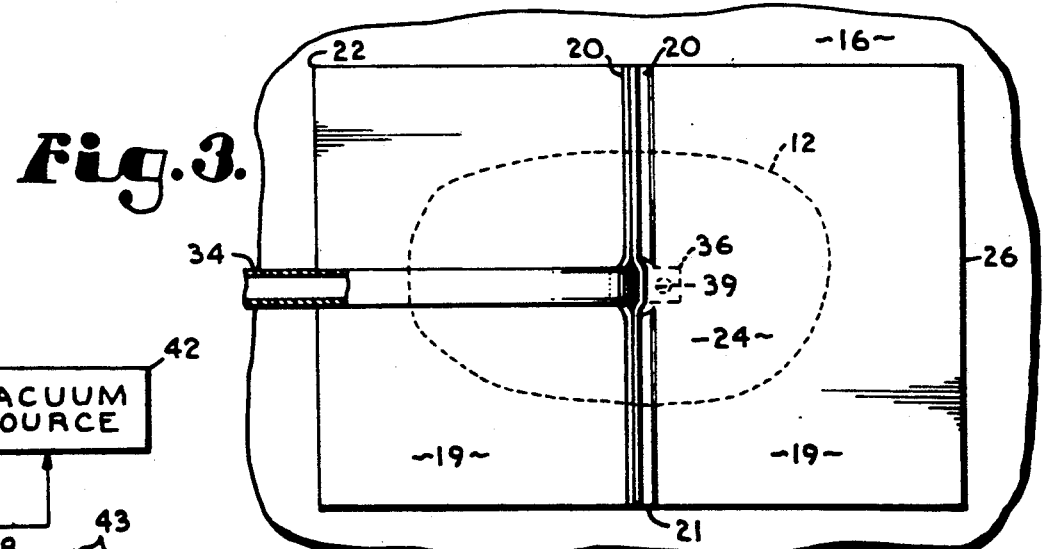
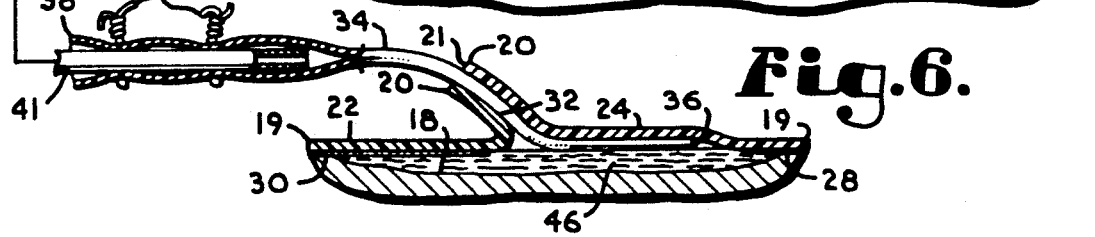

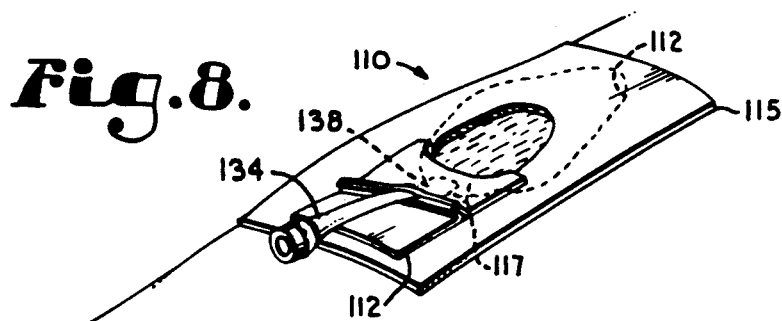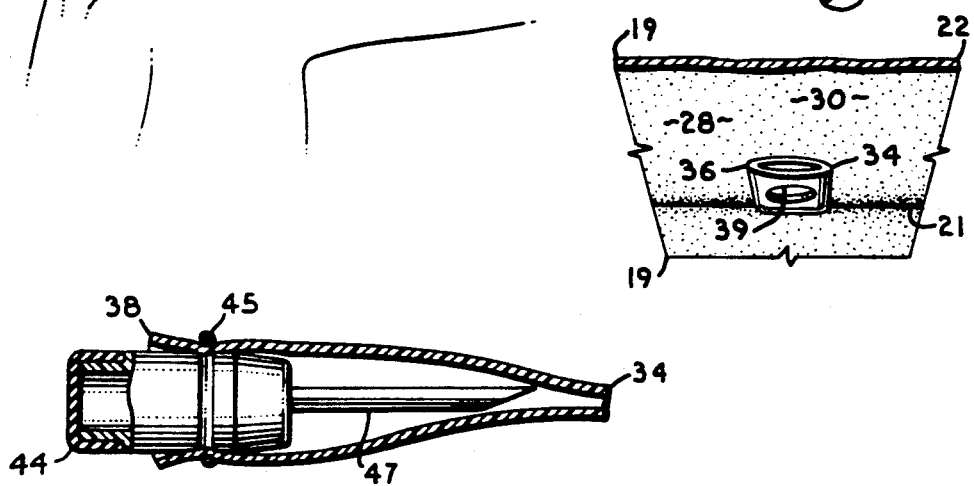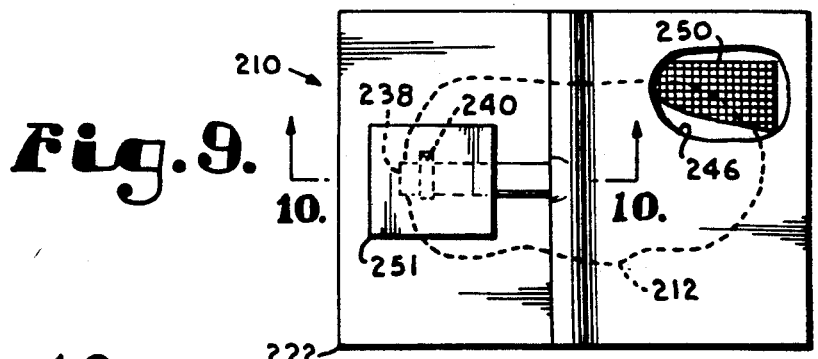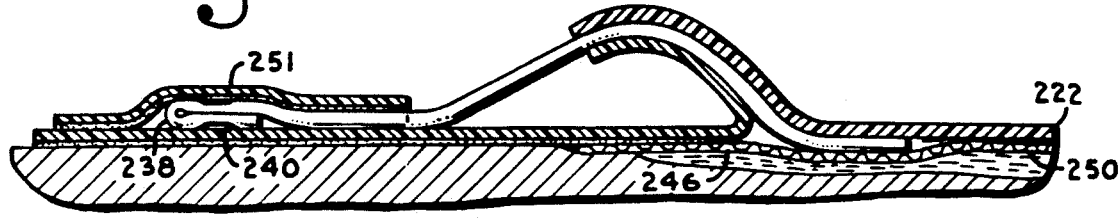

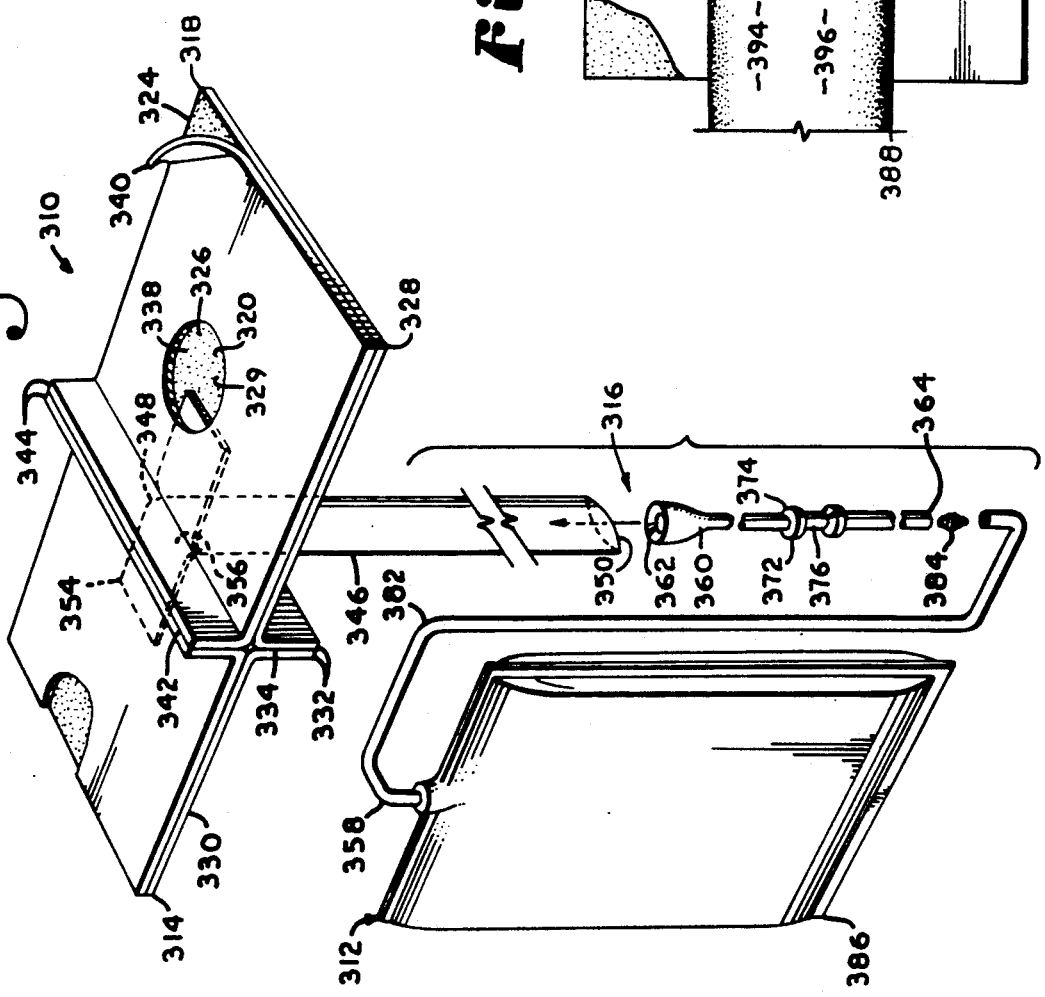
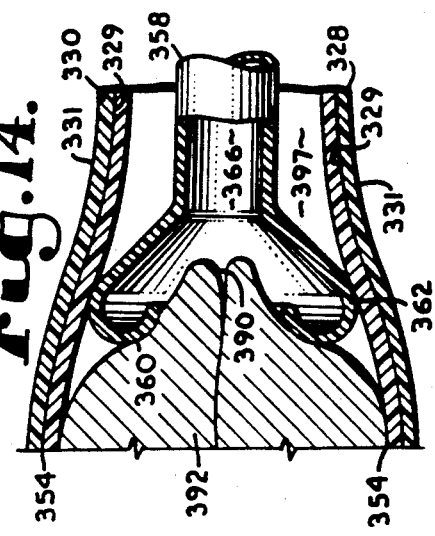
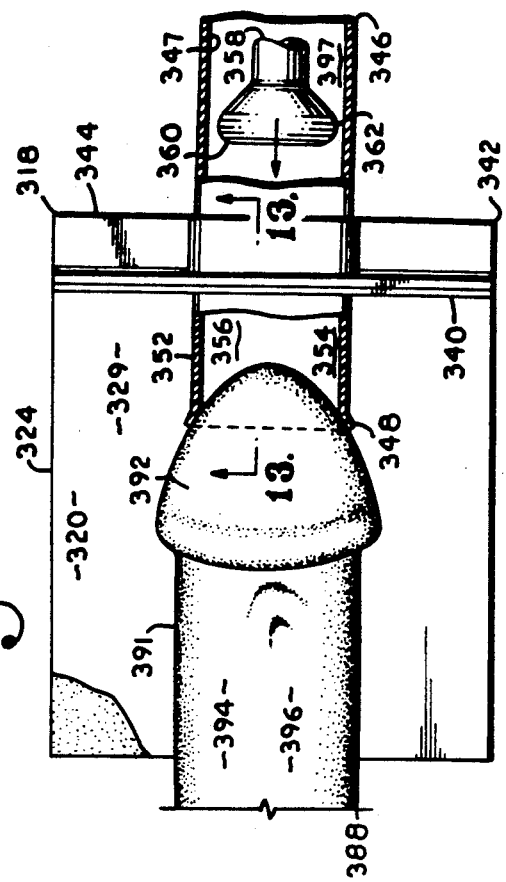

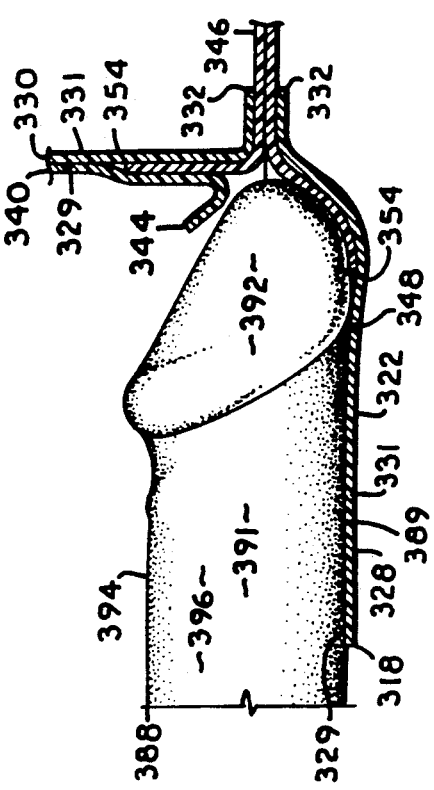
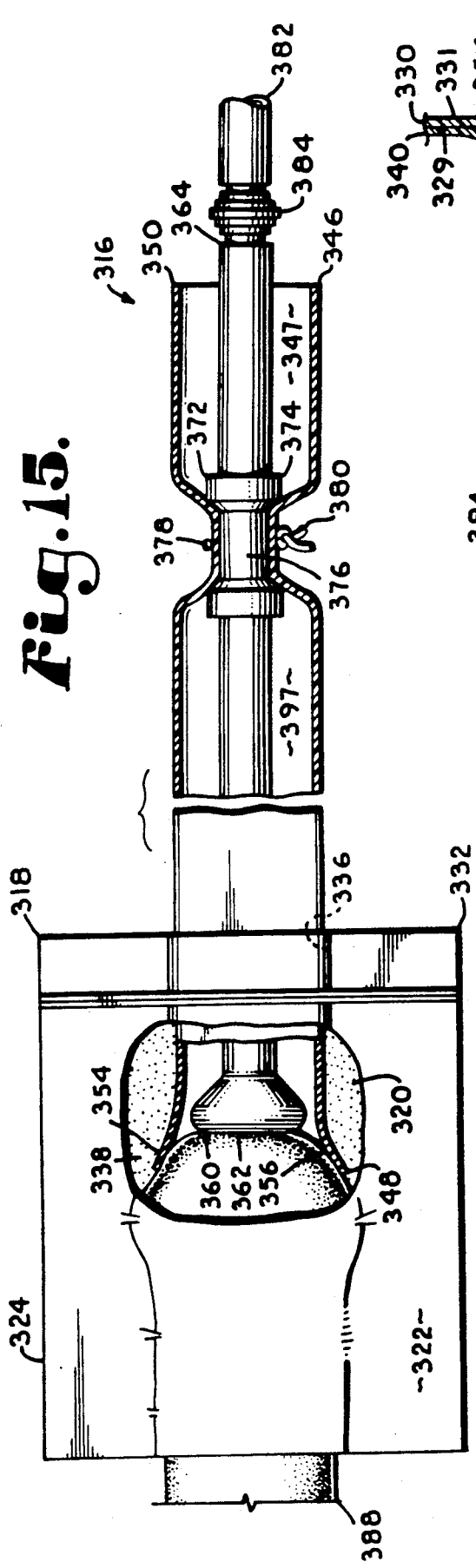
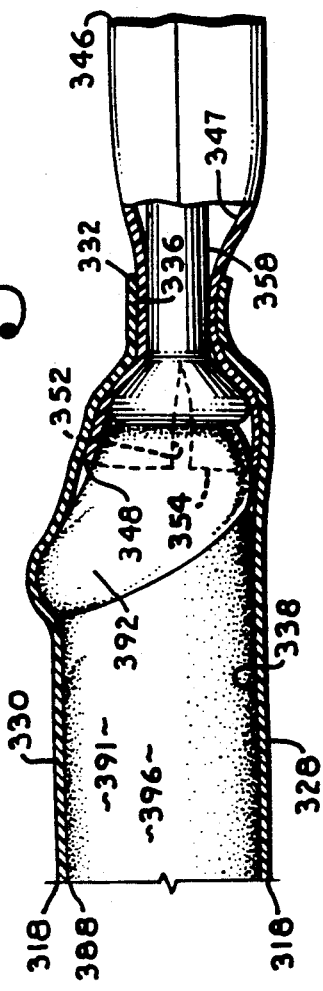

FLUIDIC CONNECTION SYSTEM AND METHOD

CROSS-REFERENCE TO RELATED APPLICATION

Continuation-in-part of U.S. patent application Ser. No. 07/332,699, filed Apr. 3, 1989, now U.S. Pat. No. 4,969,880 issued 11/13/90.

BACKGROUND OF THE INVENTION

1. Field of the Invention

The present invention relates generally to fluidic connection systems, and in particular to systems for draining liquids from and introducing liquids to patients.

2. Description of the Relevant Art

Various types of fluidic connection systems have heretofore been devised to meet the requirements of particular applications. In the medical field, fluidic connection systems find many applications, including wound dressings and systems for introducing fluids to and removing fluids from patients.

Wound dressings are typically applied over various types of wounds to promote healing and to reduce the risk of infection. Although various types of dressing materials have been successfully employed, membranes comprising semi-permeable materials are often preferred because they can increase patient comfort and lower the risk of infection. Semi-permeable membranes generally pass moisture vapors, but are generally impervious to liquids. Thus, they can promote healing by permitting a wound site to "breathe".

However, a problem can arise with semi-permeable membranes when they are placed over draining wounds because they tend to retain fluid. For example, surgical wounds often tend to drain for a post-operative period of about forty-eight hours. The fluid that can accumulate under such a semi-permeable membrane during a draining period can macerate the underlying tissue, cause infection and otherwise inhibit healing. A procedure for alleviating this problem involves periodically piercing the membrane, draining the accumulated fluids and resealing the membrane opening. However, such a procedure is time-consuming for health care professionals and, unless it is conducted at relatively frequent intervals, can be relatively ineffective in dealing with the problems associated with trapped fluid accumulation. Other procedures which involve opening or changing wound dressings tend to have problems associated with exposing a wound to a greater risk of infection and can be uncomfortable for patients.

Another disadvantage with many previous wound dressings is that they are not designed to accommodate the introduction of various liquid medications, such as antibiotics and growth factor solutions. The application of growth factor solutions may be particularly important in the regeneration of skin graft donor sites.

Catheters are another type of fluidic connection system with medical applications. They are commonly used for withdrawing fluids from or introducing fluids to patients' bodies. For example, urethral catheters are inserted into the bladder through the urethra for withdrawing urine. Typical applications for urethral catheters include patients who are incontinent or have otherwise lost voluntary control of their bladder functions, e.g. a paraplegic with a spasdic bladder condition. However, patients fitted with urethral catheters are often subjected to risks of bladder and urinary tract infections.

To avoid some of these infection risks, condom catheters have been devised which typically include a body for placement over the penis and a bellows-type distal end for resisting kinks and for connection to a drain tube. However, condom catheters are susceptible to slippage and can be difficult to maintain in place unless they are taped to the patient's penis. Furthermore, there can be difficulties in effectively draining sudden surges of urine, which often back up and cause leakage problems.

Heretofore there has not been available a fluidic connection system and method with the advantages and features of the present invention.

SUMMARY OF THE INVENTION

In the practice of the present invention, a fluidic connection system is provided which includes a semi-permeable membrane including a pair of panels each having a perimeter and an edge strip. The membrane is formed by connecting the panel edge strips together to form a seam extending transversely across the membrane. The panels and the membrane include inner and outer surfaces. A tube opening extends through the seam between the panel edge strips and between the membrane inner and outer surfaces. The membrane inner surface is coated with an adhesive for attachment to the skin of a patient.

A tube or sheath includes a proximate end extending through the tube opening and a distal end positioned in spaced relation from the membrane outer surface. In one embodiment, the tube proximate end includes a side opening which is positioned in proximity to the membrane inner surface. In another embodiment the tube proximate end is bifurcated by a pair of longitudinally-extending slits separating a pair of tabs. A passage extends through the sheath between its ends.

An inner conduit can be placed in the sheath passage and can include a connection seal assembly for forming a fluid-tight seal with the sheath. The inner, tubular conduit can be provided with a funneled proximate end for using the system as a condom catheter.

When the fluidic connection system is used as a wound dressing, an intermediate layer of material can be applied between the wound and the cover membrane inner surface. Furthermore, the fluidic connection system of the present invention can be used to secure a percutaneous drainage tube within a patient, e.g. by inserting the percutanious tube through the sheath passage.

In the practice of the method of the present invention, an intermediate layer of material can be applied to a wound site and the cover membrane can then be placed thereover. The cover membrane can be releasably, adhesively fastened to the skin around a periphery thereof. A tube fluidically communicates with the wound through an opening in the membrane. Fluids from a draining wound can be evacuated through the tube and liquid medication and irrigation can be introduced through the tube to the wound site. The fluid evacuation and introduction steps of the method can each be accomplished both actively and passively, and can be alternated in a wound treatment procedure. Additional steps that can be included in the method of the present invention include extending an inner conduit through the sheath and sealing the inner conduit and the sheath together in a fluid-tight engagement.

OBJECTS AND ADVANTAGES OF THE PREFERRED EMBODIMENTS

The principle objects and advantages of the present invention include: to provide a wound dressing; to provide such a dressing which promotes the evacuation of drainage fluids; to provide such a dressing which permits the introduction of liquid medications; to provide such a dressing which includes a semi-permeable membrane for releaseable, adhesive attachment to the skin surface surrounding a wound; to provide such a dressing which protects against infection; to provide such a dressing which promotes healing; to provide such a dressing which is economical to manufacture, efficient in operation, capable of a long operating life and particularly well adapted for the proposed usage thereof; to provide a wound treatment method; to provide a fluidic connection system and method; to provide such a connection system and method which are adaptable to various applications; to provide such a connection system and method which can be utilized as a condom catheter; to provide such a connection system and method which are suitable for securing percutanious tubing; to provide such a connection system which infrequently requires changing; and to provide such a connection system and method which promote patient comfort, reduce risk of infection, are usable with catheters of various configurations and which are easy to apply and use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a top perspective view of a wound dressing embodying the present invention.

FIG. 2 is an enlarged, vertical, cross-sectional view of the dressing taken generally along line 2—2 in FIG. 1.

FIG. 3 is a top plan view of the dressing.

FIG. 4 is an enlarged, fragmentary, bottom perspective view of the dressing, particularly showing a proximate end of the tube.

FIG. 5 is an enlarged, fragmentary, top perspective view of the dressing, particularly showing a tube closure clip.

FIG. 6 is an enlarged, fragmentary, vertical, cross-sectional view of the dressing, particularly showing the tube connected to a vacuum source.

FIG. 7 is an enlarged, fragmentary, vertical, cross-sectional view of the dressing, particularly showing a resealable injection port mounted on a distal end of the tube.

FIG. 8 is a top perspective view of a wound dressing comprising a first modified embodiment of the present invention.

FIG. 9 is a top plan view of a wound dressing comprising a second modified embodiment of the present invention with an intermediate material layer between the wound site and a cover membrane.

FIG. 10 is an enlarged, fragmentary, vertical, cross-sectional view of the second modified wound dressing embodiment, taken generally along line 10—10 in FIG. 9.

FIG. 11 is a perspective view of a fluidic connection system comprising a third modified embodiment of the present invention, shown in combination with a drain conduit and fluid connection vessel for use as a condom catheter and urine collection system.

FIG. 12 is a top plan view of the connection system being applied as a condom catheter.

FIG. 13 is an enlarged, vertical, cross-sectional view of the connection system taken generally along line 13—13 in FIG. 12.

FIG. 14 is an enlarged, fragmentary, vertical, cross-sectional view of the connection system, particularly showing a funnel end of an inner conduit.

FIG. 15 is a top plan view of the connection system.

FIG. 16 is a side elevational view of the connection system.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience and reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the structure being referred to. Said terminology will include the words specifically mentioned, derivatives thereof and words of similar import.

Referring to the drawings in more detail, the reference numeral 10 generally designates a wound dressing embodying the present invention. The dressing 10 is adapted for protecting and treating a variety of wounds, such as that shown at 12. Without limitation on the generality of the useful applications of the present invention, the dressing 10 may be applied over burns, cuts, scrapes and ulcers of various types, e.g. diabetic, decubitus, peripheral vascular disease, venous stasis and trauma ulcers.

Skin ulcers are a common problem among many diabetics, and are often brought on by poor blood circulation and nerve damage associated with diabetes. The treatment of such ulcers often involves grafting skin from a relatively healthy donor site to an ulcerous wound site. Split thickness surgical skin graft techniques may be employed to obtain skin grafts from donor sites that can then heal spontaneously. Full thickness skin grafts, on the other hand, generally require closure of the donor site. It will be appreciated from the following description that the wound dressing and treatment method of the present invention is particularly well adapted for the protection and regeneration of skin graft donor sites by providing a single dressing which facilitates both fluid drainage and growth factor introduction.

The wound site 12 is surrounded by healthy skin 16. A fibrin layer 18 forms at the wound site 12 from fibrinogen by the action of thrombin and the clotting of blood (FIGS. 2 and 6). Surgical wounds, including those associated with skin grafts, normally drain fluid. The fluid drainage from a surgical wound is generally heaviest during a post-operative period of about forty-eight hours.

II. Wound Dressing 10

The wound dressing 10 generally comprises a cover membrane 22 with an interior portion 24 surrounded by a perimeter 26. The membrane 22 includes a skin contact surface 28 with an adhesive coating 30. The membrane 22 preferably comprises a breathable semi-permeable material characterized by an ability to pass moisture vapors and an imperviousness to liquids. The adhesive coating 30 should likewise be semi-permeable. Such membrane materials are commercially available, an example being material referred to as "Tagoderm", which is available from the 3M (Minnesota Mining and Manufacturing) Company of St. Paul, Minn. Other semi-permeable materials are available and can be successfully employed with the present invention. A protective backing 23 is placed over the adhesive coating 30 on the membrane skin contact surface 28 until the membrane 22 is ready for application.

The membrane 22 comprises a pair of panels 19 with inner, upturned edges 20 which can be adhesively joined together to form a seam 21 which extends transversely across the membrane 22 and projects generally upwardly therefrom. The panels 19 can be secured together at the seam 21 by the adhesive coating 30 to form the seam 21.

A tube or sheath 34 includes a proximate end 36 located under the membrane 22 and a distal or free end 38. The tube 34 can be inserted through the seam 21 which forms an opening 32 between the panel edge strips 20 at approximately the center of the membrane 22. A relatively short length of the tube 34 adjacent to its proximate end 36 is shown under the membrane 22, but greater lengths of the tube 34 could be placed under the membrane 22. As shown in FIG. 5, the tube proximate end 36 is open, and adjacent to the proximate end 36 an opening is formed. Preferably the tube opening 39 projects downwardly, i.e. away from the membrane skin contact surface 28. The short length of the tube 34 which is located under the membrane 22 can be releaseably secured to the skin contact surface 28 by the adhesive coating 30, preferably with the tube opening 39 facing downwardly.

The tube 34 can comprise, for example, a flexible, plastic tube of the type that is commonly used as a protective sheath for protection of sterility for percutaneous intravenous catheter placement. Such sheaths are commercially available from Aero Internaional, Inc. of Reading, Pa.

At its distal end 38, the tube 34 is adapted for: 1) closure with a variety of suitable closure devices; 2) connection to various active and passive fluid collection devices for draining and evacuating fluid from the wound site; and 3) connection to various fluid source devices for actively and passively introducing fluid to the wound site.

FIG. 5 shows a bifurcated clip 40 for releaseably closing and sealing the tube distal end 38, which is folded upon itself as shown.

FIG. 6 shows a vacuum tube end 41 inserted in the tube distal end 38 and secured therein by ties or ligatures 43. The vacuum tube 41 fluidically communicates with a suction or vacuum source 42 for actively draining fluid from the wound site. The suction or vacuum source 42 may comprise a relatively simple, hand-actuated bulb or bellows, or it may comprise a more sophisticated motorized pump which can be actuated at predetermined time intervals or in response to wound site conditions such as an accumulation of fluid under the membrane 22.

FIG. 7 shows an injection port 44 sealed to the tube distal end 38 by a band 45. The injection port 44 includes a sleeve 47 which can extend into the tube 34 to protect it from needle puncture. The injection port 44 can be of the type which is designed for reuse and which automatically reseals after being punctured by a syringe needle. It will be appreciated that a wide variety of devices can be employed for connecting the tube distal end 38 to various liquid medication sources.

III. Treatment Method

According to the treatment method of the present invention, the protective backing 23 is removed from the membrane contact surface 28 to expose the adhesive coating 30 and the membrane 22 is placed over a wound site 12 with its contact surface 28 down. The membrane perimeter 26 is pressed against the healthy skin 16 surrounding the wound site 12 to preferably form a relatively liquid-tight adhesive bond therebetween. Various adhesive preparations are commercially available for supplementing the bonding action of the adhesive coating 30 in bonding the membrane contact surface 28 to the healthy skin 16. The membranes 22 may be provided in various sizes to accomodate wounds of different sizes. A sufficiently large membrane 22 should normally be selected to provide ample overlap of the perimeter 26 over the healthy skin 16 to insure a good bond therebetween.

The tube distal end opening 39 may be placed directly over the approximate center of the wound site 12, or it may be placed eccentrically or at a depending location with respect to the wound site 12. A dependent or lower position for the opening 39 with respect to the wound site 12 may be preferred to facilitate fluid drainage. The dressing 10 may be applied promptly after a wound is inflicted, e.g. immediately after the graft removal procedure and a skin graft operation. To reduce the risk of infection, it may be advisable to promptly cover the open wound site 12. The wound dressing 10 may be kept in a sterile package until it is needed. Such sterile packages and packaging techniques are well known. For example, ethylene oxide may be used to sterilize the dressing 10 prior to placement in a suitable sterile package. The protective backing 23 is removed from the membrane 22, thereby exposing its adhesive-coated contact surface 28.

With the membrane 22 thus secured, a chamber 46 is formed between the wound site 12 and the membrane contact surface 28, and is surround by the membrane perimeter 26. The chamber 46 fluidically communicates with the membrane opening 32. In an evacuation mode of operation, such as might be desirable for forty-eight hours or so after removal of a split-thickness skin graft at a donor site, fluid 20 which accummulates in the chamber 46 is communicated through the opening 32 and thence through the tube 34 for collection and disposal. In a passive evacuation mode of operation, the fluid 20 is evacuated through capillary action, or by gravity with the opening 32 at a dependent, lower location in relation to the wound site 12. Such a capillary, passive drainage action may be sufficient for draining the wound site 12 in many situations. Alternatively, an active evacuation mode of operation involves attaching the tube 34 to the suction/vacuum source 42 whereby the fluid 20 is positively drawn from the wound site 12 and the chamber 46. Such an active evacuation mode of operation may be preferred when the dressing 10 is used in connection with a hydrophilic colloidal material (hydrocolloid), as will be explained in more detail hereinafter.

It may be desirable to operate the wound dressing 10 in an introduction mode of operation whereby medications such as antibiotics and growth factor solutions are introduced to the wound site 12. In this mode of operation, the tube distal end 38 is connected to a liquid solution source, which may comprise a syringe or any of various liquid containers for passive, gravity-induced introduction. Various adaptors, valves and injection needle ports are available for fluidically coupling the tube 34 to a wide variety of liquid solution sources. For example, many such connectors and adaptors are available from Aero International, Inc. of Reading, Pa. Such connecting devices are commonly used in connection with the intravenous introduction of various liquid solutions.

In an active introduction mode of operation, solutions may be pumped through the tube 34 into the chamber 46 for application to the wound site 12.

The evacuation and introduction treatment steps can be timed and sequenced as necessary to achieve the treatment objectives. For example, treatment of a skin graft donor site may involve fluid withdrawal and drainage for about two days immediately following the skin graft operation, followed by treatment steps comprising the introduction of antibiotics and/or growth factor solutions to the wound site. The evacuation and introduction steps can be alternated, and the intervals between such steps can be progressively increased or decreased as necessary to facilitate healing. As the wound heals, progressively smaller amounts of fluid will ooze therefrom and the frequency and duration of the drainage operations can be correspondingly reduced and finally discontinued altogether.

It will be appreciated that the wound dressing and treatment method of the present invention are broadly concerned with introducing fluid to wound sites and evacuating fluid therefrom. The fluid introduction and evacuation procedures described herein can be performed indefinitely without having to change the dressing 10. The tube 34 cooperates with the membrane 22 to permit the same dressing 10 to be used for both procedures, which may be alternated as often as necessary. Infection risks and patient discomfort can be reduced by minimizing wound dressing changes.

The removal of toxins and bacteria from wounds is an important aspect of the fluid drainage phase of the healing process. The wound dressing of the present invention facilitates removal of serum and other secretions to minimize the risk of infecting the wound site and macerating the tissue thereat. Growth factor solutions can be important in promoting healing, and antibiotics can be important in preventing and treating infection. Hence, a comprehensive wound treatment can be implemented with the wound dressing and treatment method of the present invention.

The wound dressing 10 can be employed to irrigate a wound whereby fluid is introduced and then removed.

The operation of the wound dressing 10 is largely a matter of fluid mechanics, and the function of the wound dressing 10 would probably be determined by such factors and variables as: 1) fluid viscosity; 2) permeability of the membrane 22; 3) cross-sectional area of the tube 34 and the area of its opening 39; 4) the integrity of the seal around the membrane perimeter 26; 5) the drawing power of the suction or vacuum source 42; 6) coagulation of the serum or other fluid; 7) the area of the fluid collection chamber 46; 8) the length of the tube 34; and 9) gravity and the relative positions o various components. Naturally, varying one or more of these factors or variables could change the operation of the system. It is anticipated that, applying such well-known principles of fluid mechanics, all of the wound dressing components could be properly sized and designed. For example, the tube opening 39 could be enlarged, or multiple openings could be provided to increase the rate of fluid flow into the tube 34. The rate of fluid flow can further be increased by locating the tube distal end 38 at a dependent area within the chamber 46, i.e. below the level of most of the wound site 12. The tube 34 can extend downwardly to a collection site below the level of the wound site 12 to facilitate gravity drainage.

It is further anticipated that some fluids will resist drainage because of their viscosities or because they tend to coagulate. Drainage of such fluids can be effected by irrigating the wound site 12.

IV. First Modified Embodiment 110

FIG. 8 shows a wound dressing 110 comprising a first modified embodiment of the present invention wherein a relatively small membrane 122 is provided and functions as a patch for a larger wound cover 115 with an opening 117 for receiving a distal end 138 of a tube 134. The primary wound cover 115 is selected to cover a wound site 112, and is placed thereover in the normal fashion. The wound dressing 110 can be placed on the primary wound cover 115 in a location chosen to enhance fluid introduction and/or evacuation. For example, to enhance the evacuation of fluid by gravity, it may be desirable to form the opening 117 at a relatively low position of the wound site 112. Thus, fluid will tend to flow to the tube 134 by gravity. To facility the introduction and distribution of fluid, it may be desirable to locate the wound dressing 110 at a relatively high position on the wound cover 115. In fact, two or more wound dressings 110 could be placed on a single, primary wound cover 115, with a lower wound dressing 110 being provided for fluid evacuation and an upper wound dressing 110 being provided for fluid introduction.

In the practice of the treatment method of the present invention, the wound dressing 110 provides for considerable flexibility in locating the wound dressing 110 in an appropriate location on the wound site 112. After the primary wound cover 115 is positioned, the opening 117 is formed at the chosen location and the wound dressing 110 may be applied, much like a patch, with the tube distal end 138 extending through the primary wound cover opening 117. It will be appreciated that wound dressings 110 may be changed as needed without changing the primary wound cover 115.

V. Second Modified Embodiment 210

A wound dressing 210 comprising a second modified embodiment of the present invention is shown in FIGS. 9 and 10 and includes an intermediate layer of material 250 between a wound site 212 and a cover membrane 222. The intermediate material layer 250 can comprise a variety of materials with varying properties such as: 1) absorbency; 2) wicking or capillary action; and 3) surface contact action. The intermediate material layer is primarily located in a chamber 146 formed between the wound 212 and the membrane 222.

As a first example of an intermediate material layer 250, several hydrophilic colloid materials (i.e. hydrocolloids) are available which would tend to absorb fluids. For example, Envisan wound cleaning pads and paste are available from Marion Laboratories, Inc. of Kansas City, Mo. and comprise: spherical, hydrophilic Beads of Dextranomer, 0.1 to 0.3 mm in diameter; polyethylene glycol 3000 in the pad; polyethylene glycol 600; and water QS enclosed in a polyamide net bag in the pad or available in a metal foil packet for the paste. The Envisan dextraminer beads function to absorb fluid and facilitate healing by drawing fluid from the wound. Excess fluid can be drained from the intermediate material layer 250 to prolong its effectiveness. Other hydrocolloids are commercially available and may be employed with the wound dressing 210 of the present invention, e.g. dextranimers available under the trademark "Debrisan".

Alternatively, the intermediate material layer 250 can comprise a mesh or sheet of synthetic material which is generally nonabsorbent and would tend to wick fluid from the wound site 212 to a tube distal end 238. For example, rayon available under the trademark Owens non-adherent surgical dressing from the Davis & Geck division of American Cyanamid Company of Danbury, Conn. could be used to form such an intermediate material layer 250, and material available from Marion Merrell Dow, Inc. of Kansas City, Mo. under the trademark "Envinet" could also be employed. Such materials may be referred to as "surface active", i.e. promoting fibrin sealing on the wound surface. Such materials can also satisfy a capillary purpose whereby fluid is wicked from the wound for collection in the chamber 246 and ultimately for drainage. With many such materials, a balance is struck between surface action and capillary action, i.e. one such function is often maximized at the expense of the other. For example, Owens rayon is generally considered to be relatively surface active, but may provide less capillary action than other materials. Envinet mesh, on the other hand, provides greater capillary action, but may provide less surface action as compared to the rayon material.

Other materials that can be used for the intermediate material layer 250 include polyurethane foam and polyurethane mesh.

The wound dressing 210 can be used according to methods for use with the other wound dressings 10 and 110, and includes the additional step of placing the intermediate material layer 250 over the wound site 212. It will be appreciated that there may be a number of materials suitable for the intermediate layer 250 to achieve various objectives.

A closure patch 251 is provided for placement over the tube distal end 238 and is adapted for securing it in a folded configuration to the membrane 222. The closure patch 251 can be used in conjunction with a bifurcated clip 240 as shown in FIGS. 9 and 10, and permits convenient access to the tube distal end 238 for coupling it to various devices such as those described herein, allowing future reuse of the tube or intermittent function. Alternatively, the tube can be severed at the surface of the membrane, allowing the closure patch 251 or a similar patch of the same material as the wound dressing 10 to permanently seal the tube site.

VI. Third Modified Embodiment 310

A fluidic connection system 310 comprising a third modified embodiment of the present invention is shown in FIGS. 11–16. Without limitation on the generality of useful applications of the fluidic connection system 310, it is shown in connection with a urine collection system 312 and functions as a condom catheter. The connection system 310 generally includes a membrane assembly 314 and a tube assembly 316.

The membrane assembly 314 includes a membrane 318 with an inner or skin contact surface 320, an outer surface 322, a perimeter 324 and an interior portion 326. As shown in FIG. 11, the membrane 318 comprises first and second panels 328, 330.

The panels 328, 330 include inner contact surfaces 329, outer surfaces 331, perimeters 333, and edges 335 with edge strips 332 which are joined together in opposing relation to form a seam 334 extending transversely across the membrane 318 between opposite sides of its perimeter 324. A tube opening 336 extends through the seam 334 approximately in the middle thereof and is open at the membrane inner and outer surfaces 320, 322.

An adhesive layer 338 substantially covers the membrane inner surface 320 and releasably secures a two-piece protective backing 340 (e.g. paper, plastic or some other suitable material). The backing 340 can form a transverse seam 342 with a pair of unattached edge strips 344 adapted to be grasped for pulling off the backing 340. The membrane 318 of the fluidic connection system 310 can comprise a semi-permeable material.

The tube assembly 316 includes an outer tube or sheath 346 with proximate and distal ends 348, 350 and a passage 347 extending therebetween. The proximate end 348 extends through the tube opening 336 and has a bifurcated configuration with a pair of longitudinally-extending, opposed slits 352 forming an opposed pair of tabs 354 each placed against a respective panel contact surface 320 (FIG. 11). The tabs 354 can be secured to the respective panel inner surfaces 320 by the adhesive 338 thereon. However, for many applications of the connecting system 310 it may be preferrable for the tabs 354 not to have adhesive on them. The tabs 354 form a mouth 356 open at the outer tube proximate end 348 and located adjacent to the membrane inner surface 320. The outer tube or sheath 346 can comprise a flexible, collapsible, impervious material.

The tube assembly 316 also includes an inner tube or conduit 358 with a proximate end 360 including a funnel 362, a distal end 364, and a conduit bore 366 extending between and open at the conduit ends 360 and 364.

An annular connector/seal band 372 receives the conduit 358 and includes enlarged-diameter end flanges 374 with a reduced-diameter, annular channel or waist 376 therebetween. The connector or seal band 372 can be intergally formed with the conduit and thus permanently fixed in position thereon, or, alternatively, the band 372 can slideably receive the conduit for adjustable repositioning. Preferably the band 372, in either configuration, forms a relatively fluid-tight seal on the conduit 358. The band 372, like the funnel 362, can be slid through the sheath passage 347 for placement proximal to the sheath distal end 350 (FIG. 15). Belt or tie means 378 can be provided for sealingly fastening the sheath 346 to the band 372. As shown in FIG. 15, the belt/tie means 378 can comprise ligatures 380, which can be wrapped around the sheath 346 for tightening it against the band channel 376. Belt/tie means 378 can comprise other suitable fasteners, such as strips with hook-and-loop fasteners (i.e. fasteners available under the trademark "Velcro"), rubber or elastic bands, plastic coated wire twist ties, etc. Multiple bands 372 can be used for connecting and sealing the sheath 346 and the conduit 358.

The conduit distal end can project distally from the sheath distal end 350 (FIG. 15) for connection to tubing 382 by a suitable tubing connector, such as the multi-diameter, double male-ended ("Christmas Tree") connector 384 shown in FIGS. 11 and 15. The tubing 382 can lead to a suitable fluid collection vessel 386, which can be positioned remote from the patient.

VII. Applications and Operation

The fluidic connector 310 can be utilized for a variety of fluidic connection applications without the inner tube or conduit assembly 358. For example, the fluidic connection system 310 can function as a wound dressing which operates in a manner similar to the wound dressings 10, 110 and 210 described above. In such applications the membrane 318 can comprise a semi-permeable, plastic, film adherrent dressing sheet, such as those commercially available under the trade names "Op-Site", "Tagaderm", and "Bio-Occlusive". The outer tube or sheath 346 can be utilized as a two-way conduit for draining wound exudate and for introducing liquids to the wound. The liquids introduced could comprise, for example, aqueous solutions for irrigating the wound and growth factors for promoting healing. Epidermal growth factor ("EGF") is available from Vicron. Platelet derived growth factor is available from the Curatech Corporation. Such growth factors can accelerate healing and reepithelialization of wound sites. Without limitation on a wide variety of wounds that can be treated with such dressings, they are particularly suitable for partial thickness wounds, such as skin graft donor sites. Drainage and liquid application can be alternated without having to intermittently change the membrane 318. Frequent dressing changes can be painful to skin wound patients and burdensome to health care personnel.

As with the previously described application of the wound dressing 110 shown in FIG. 8, the connection system 310 can be applied at any desired location on a larger patch or membrane, and can be used in various multiple combinations, if desired. For example, one connection system 310 can be used for introducing fluids, and another connection system 310 can be used for draining fluids, with both connection systems 310 operating simultaneously if desired.

To promote efficient drainage, the connection system 310 can be located at a dependent part of a larger dressing. Alternatively, mechanical suction equipment can be connected for promoting drainage.

Another application of the fluidic connection system 310 is placement over percutaneous catheters, drain tubes, etc. Such tubes present infection risks where they penetrate the skin surface, and can require frequent application of antibiotics to reduce the risk of infection. Percutaneous tubes are often sutured in place at the stab wound locations where they penetrate the skin, and the sutures are further susceptible to infection and can cause swelling and patient irritation. The connection system 310 can be placed over such a percutaneous drain tube or catheter site, with the tubing extending through the sheath 346 in the manner of the conduit 358. The tubing can be secured, for example with one or more bands 372, to protect against traction forces which might otherwise tend to pull the tubing loose. By utilizing a semi-permeable, breathable material for the membrane 318, the skin surrounding a percutanious tubing entry site can be protected against maceation.

For use as a condom catheter in a urine collection system 312, the backing 340 can be removed from the first panel 328, which is then adhesively secured to the ventral side 389 and the lateral sides 391 of a flaccid penis 388 with the urethra orifice or meatus 390 directed at the sheath mouth 356 and the sheath tabs 354 placed on the top and bottom of the glans or penile head 392 (FIG. 13). The second panel 330, with the backing 340 removed, can then be adhered to the penile dorsal side 394 and to the first panel 328.

The procedure described above provides a relatively secure attachment of the connection system 310 to the penis 388, since the penile shaft 396 and the penile head 392 provide substantial areas of attachment. The attachment can further be enhanced by prestretching the flaccid penis to provide maximum contact area.

The connection system 310 described above can be utilized as a complete condom catheter by fluidically connecting the sheath distal end 350 to a suitable urine vessel, for example with a band such as that shown at 45 in FIG. 7. Alternatively, the inner tube or conduit 358 can then be inserted through the sheath passage 347 in its open, distal end 350. The funnel 362 can be placed against the glans 392 over the meatus 390, and can be secured in this position by fastening the sheath 346 to the band 372 with the sheath 346 slightly in tension and the conduit 358 slightly in compression. The funnel 362 can comprise a moldable plastic material, and its end can be rolled or flanged as shown in FIG. 14 for patient comfort. However, in operation the funnel 362 is not required to form a fluid-tight seal with the glans 392, and it is anticipated that the funnel 362 may slip distally away from the glans 392. The funnel 362 cooperates with the connection system 310 to direct a surge of urine into the conduit 358. Urine which escapes the funnel 362 can collect in an interstitial space 397 between the sheath 346, the conduit 358, the glans 392 and the band 372. Urine in the interstitial space 397 can drain to the funnel 362 for evacuation through the conduit 358. Placement and sizing of the sheath 346, the conduit 358 and the band 372 can be adjusted to vary the volume of the interstitial space 397.

The procedure for applying the connection system 310 can be varied according to the conditions of particular patients and the preferences of persons applying it. Properly adherred to a patient, the collection system 310 should be functional for a relatively long period of time, and a semi-permeable membrane material can be utilized to enhance patient comfort.

Other useful applications of the connection system 310 include placement over circumferentially injured limbs and phalanges for draining exudates and/or introducing liquids. For example, an injured hand could be treated by securing the connection system 310 at the wrist, a forearm could be treated by adhering the fluidic connection system 310 at the elbow, etc.

Yet another application is for accessory connections whereby various fluid devices and connectors could be combined in systems attached to patients for appropriate treatment and diagnostic procedures. Such additional accessories include Jackson-Pratt and Blake suction tubing devices, Y-connectors, sampling ports, "Injectaport" devices, fluid pumps and various fluid reservoirs. Hand-actuated bulbs could be placed in the tubing, and valving could be placed where it is needed.

A further application of the fluidic connection system 310 would involve placing the membrane 318 over an intermediate material layer 250 as described in connection with the wound dressing 210 comprising a second modified embodiment of the present invention (FIGS. 9 and 10). An inner tube or conduit such as that shown at 358 could then be extended through the sheath 346, secured thereto by a band or bands 372, and the inner tube or conduit distal end 364 could be placed beneath the intermediate material layer 250 adjacent to the tissue surface at the wound site 212, or the conduit distal end 364 could be embedded within the intermediate material layer 250. The inner tube or conduit 358 could then be used for draining exudate from or introducing fluids to the wound 212.

It is to be understood that while certain forms of the present invention have been illustrated and described herein, it is not to be limited to the specific forms or arrangement of parts described and shown.

What is claimed and desired to be secured by Letters Patent is as follows:

1. A fluidic connection system which comprises:
   (a) covering means with a contact surface and an outer surface;
   (b) adhesion means for releasably attaching said covering means on said contact surface thereof;
   (c) said covering means having an interior portion with an opening extending between and open at said contact and outer surfaces thereof;
   (d) said covering means comprising a semi-permeable material; and
   (e) tube means having a proximate end fluidically communicating with said opening adjacent said contact surface and a distal end located outwardly from said outer surface, said tube means fluidically communicating with said contact surface.

2. The invention of claim 1 wherein said covering means includes:
   (a) first and second panels each having a perimeter and an edge;
   (b) each said panel having an inner contact surface and an outer surface;
   (c) a seam extending transversely across said connection system and extending outwardly from said outer surfaces of said panels, said seam comprising said panels being connected together at their respective contact surfaces adjacent to their respective edges and said seam having opposite ends; and
   (d) said tube opening extending through said seam between said panel contact surfaces and intermediate said seam ends, said tube opening extending between and open at said adjacent panel edges and at said contact surfaces.

3. The invention of claim 1 wherein said adhesion means comprises an adhesive coating on said contact surface.

4. The invention of claim 1 wherein said tube means comprises a flexible, collapsible material.

5. The invention of claim 1 wherein said tube means proximate end includes:
   (a) an opposed pair of longitudinally-extending slits; and
   (b) a pair of opposed end tabs each formed between said slits, said tube means proximate end being open between said tabs.

6. The invention of claim 5 wherein:
   (a) each said tab is adhesively connected to said contact surface.

7. A fluidic connection system, which comprises:
   (a) covering means with a contact surface and an outer surface, said covering means including:
      (1) first and second panels each having a perimeter and an edge;
      (2) each said panel having inner contact surface and an outer surface;
      (3) a seam extending transversely across said connection system and extending outwardly from said outer surfaces of said panels, said seam comprising said panels being connected together at their respective contact surfaces adjacent to their respective edges and said seam having opposite ends; and
      (4) a tube opening extending through said seam between said panel contact surfaces and intermediate said seam ends, said tube opening extending between and open at said adjacent panel edges and at said contact surfaces;
   (b) adhesion means on said contact surface for releasably attaching said covering means;
   (c) said covering means having an interior portion with an opening extending between and open at the contact and outer surfaces thereof; and
   (d) tube means having a proximate end extending through said opening and terminating adjacent said contact surface and a distal end located outwardly from said outer surface, said tube means fluidically communicating with said contact surface.

8. The invention of claim 7 wherein said covering means comprises a semi-permeable material.

9. The invention of claim 7 wherein said tube means includes:
   (a) an outer, tubular sheath connected to said panels at said seam and having a proximate end, a distal end, and a sheath passage extending between said sheath proximate and distal ends; and
   (b) an inner, tubular conduit extending through said sheath passage and including conduit proximate and distal ends and a conduit bore extending between said conduit ends.

10. A fluidic connection system which comprises:
   (a) covering means with a contact surface and an outer surface;
   (b) adhesion means on said contact surface for releasably attaching said covering means;
   (c) said covering means having an interior portion with an opening extending between and open at the contact and outer surfaces thereof; and
   (d) tube means having a proximate end extending through said opening and terminating adjacent said contact surface and a distal end located outwardly from said outer surface, said tube means fluidically communicating with said contact surface, said tube means including:
      (1) an opposed pair of longitudinally-extending slits; and (2) a pair of opposed end tabs each formed between said slits, said tube means proximate end being open between said tabs.

11. A fluidic connection system, which comprises:
(a) covering means with a contact surface and an outer surface;
(b) adhesion means for releasably attaching said covering means on said contact surface thereof;
(c) said covering means having an interior portion with an opening extending between and open at the contact and outer surfaces thereof;
(d) tube means having a proximate end extending through said opening and terminating adjacent said contact surface and a distal end located outwardly from said outer surface, said tube means fluidically communicating with said contact surface;
(e) said covering means including first and second panels interconnected at a seam; and
(f) said tube means including:
   (1) an outer, tubular sheath connected to said panels at said seam and having a proximate end, a distal end, and a sheath passage extending between said sheath passage extending between said sheath proximate and distal ends; and
   (2) an inner, tubular conduit extending through said sheath passage and including conduit proximate and distal ends and a conduit bore extending between said conduit ends.

12. The invention of claim 11 wherein:
(a) said conduit includes funnel means at its proximate end, said funnel means being adapted to slide longitudinally through said sheath passage.

13. The invention of claim 11 wherein said tube means includes:
(a) tube clamp means clamping said sheath to said inner conduit.

14. The invention of claim 13 wherein said tube clamp means comprises:
(a) an annular band with enlarged proximate and distal ends, a bore extending between said ends and a reduced-diameter waist between said ends, said bore receiving said conduit; and
(b) belt means circling said sheath and securing said sheath to said band waist.

15. The invention of claim 14 wherein:
(a) said belt means comprises a tensile member wrapped around said sheath and said band waist.

16. The invention of claim 14 wherein:
(a) said belt means comprises a strap with hook-and-loop fasteners.

17. A fluidic connection system which comprises:
(a) covering means including:
   (1) an inner contact surface;
   (2) an outer surface;
   (3) a first panel including a perimeter and an edge;
   (4) a second panel including a perimeter and an edge;
   (5) each said panel having an inner contact surface and an outer surface;
   (6) a seam extending transversely across said connection system and comprising said panels being connected together at their respective edges, said seam having opposite ends; and
   (7) a tube opening extending through said seam between said panel contact surfaces and intermediate said seam ends, said tube opening extending between and open at said adjacent panel edges and at said contact surfaces;
(b) an adhesive coating on said panel contact surfaces; and
(c) tube means including:
   (1) a proximate end extending through said tube opening and terminating adjacent said skin contact surface, said proximate end having an opposed pair of longitudinally-extending slits and a pair of opposed end tabs each formed between said slits, said tube means proximate end being open between said tabs.

18. The invention of claim 17 wherein said tube means includes:
(a) an outer, tubular sheath connected to said panels at said seam and having a proximate end, a distal end, and a passage extending between said sheath proximate and distal ends; and
(b) an inner, tubular conduit extending through said sheath passage and including conduit proximate and distal ends and a conduit bore extending between said conduit ends.

19. The invention of claim 18 wherein:
(a) said conduit includes funnel means at its proximate end, said funnel means being adapted to slide longitudinally through said sheath passage.

20. The invention of claim 18 wherein said tube means includes:
(a) tube clamp means clamping said sheath to said inner conduit.

21. A condom catheter for attachment to a penis, which includes:
(a) a membrane including:
   (1) an inner, skin contact surface;
   (2) an outer surface;
   (3) a first panel including an edge strip and a perimeter;
   (4) a second panel including an edge strip and a perimeter;
   (5) a seam extending transversely across said membrane and comprising said panel edge strips attached together; and
   (6) a tube opening extending through said seam between said membrane inner and outer surfaces;
(b) adhesive on said panel inner contact surfaces; and
(c) tube means including a proximate end extending through said tube opening and a distal end, said tube means including a passage extending between and open at said ends.

22. The invention of claim 21 wherein said tube means includes:
(a) opposed pair of longitudinally-extending slits at said proximate end;
(b) an opposed pair of tabs formed between said slits, each said tab being adhered to a respective panel inner contact surface; and
(c) a mouth open between said tabs at said tube means proximate end.

23. The invention of claim 22 wherein said tube means includes:
(a) an outer sheath comprising a flexible, collapsible material and having proximate and distal ends with a passage extending therebetween;
(b) an inner, tubular conduit extending through said sheath passage and including conduit proximate and distal ends and a conduit bore extending between said conduit ends;
(c) an annular band with enlarged proximate and distal ends and a bore extending between said end, said bore receiving said conduit and a reduced-diameter waist between said ends; and (d) belt means circling said sheath adjacent to its distal end and securing said sheath to said band waist.

24. A method of catheterizing a penis, which comprises the steps of:

(a) adhering a membrane comprising first and second panels each including a skin contact surface, an outer surface and a perimeter with an edge to the penis;

(b) forming a seam with opposite ends and extending transversely across said membrane by adhesively engaging said panel contact surfaces along respective strips adjacent to said edges thereof;

(c) providing an opening open at said panel edges and at said contact surface between said interconnected strips and intermediate said seam opposite ends;

(d) extending a sheath with a proximate end having an opposed pair of longitudinally-extending slits forming an opposed pair of tabs through said tube opening;

(e) positioning a mouth open to a passage of said sheath and formed between said tabs at said seam adjacent to said skin contact surfaces; and (f) placing said tube mouth distal to and approximately in alignment with the meatus of said penis.

25. The invention of claim 24, which includes the further steps of:

(a) extending a conduit with proximate and distal ends and a bore extending therebetween through said sheath passage;

(b) placing said conduit proximate end in proximity to and in alignment with said meatus; and (c) fluidically sealing said sheath to said conduit.

26. The invention of claim 24, which includes the further steps of:

(a) adhering said first panel to the ventral side of said penis;

(b) adhering said second panel to the dorsal side of said penis; and (c) adhering said first and second panels to each other.

27. The invention of claim 25, which includes the additional steps of:

(a) providing a funnel on said conduit proximate end; and (b) placing said funnel against the head of said penis in covering relation over said meatus.

28. A condom catheter for attachment to a penis, which includes:

(a) a membrane including:
  (1) penis contact surface;
  (2) an outer surface;
  (3) means for releasably attaching said membrane to said penis;
  (4) an interior, glans-contact portion; and
  (5) an opening extending between and open at said glans-contacting portion and said outer surface;

(b) said membrane comprising a semi-permeable material; and (c) tube means including a proximate end extending through said opening and terminating adjacent said glans-contacting portion and a distal end located outwardly from said outer surface, said tube means including a passage extending between and open at said ends.

29. A method of catheterizing a penis, which comprises the steps of:

(a) releasably adhering a semi-permeable membrane including a penis contact surface with a glans-contacting portion and an outer surface to the penis;

(b) providing a opening open at said glans-contacting portion of said penis contact surface and at said outer surface;

(c) providing tube means with a proximate end communicating with and terminating adjacent said glans-contact portion opening;

(d) providing said tube means with a distal end in spaced relation from said membrane outer surface;

(e) providing a passage through said tube means between and open at its proximate and distal ends; and (f) placing said proximate tube means end in proximity to and generally aligned with the meatus of said penis.

* * * * *